(12) United States Patent
Prutchi et al.

(10) Patent No.: US 11,582,612 B2
(45) Date of Patent: Feb. 14, 2023

(54) POWER COUPLING MODULATION TRANSMISSION

(71) Applicant: Impulse Dynamics NV, Willemstad (CW)

(72) Inventors: David Prutchi, Voorhees, NJ (US); Jason Meyers, Haddonfield, NJ (US)

(73) Assignee: Impulse Dynamics NV, Willemstad (CW)

( * ) Notice: Subject to any disclaimer, the term of this patent is extended or adjusted under 35 U.S.C. 154(b) by 8 days.

(21) Appl. No.: 16/973,822

(22) PCT Filed: Jun. 12, 2019

(86) PCT No.: PCT/IB2019/054909
§ 371 (c)(1),
(2) Date: Dec. 10, 2020

(87) PCT Pub. No.: WO2019/239343
PCT Pub. Date: Dec. 19, 2019

(65) Prior Publication Data
US 2021/0377740 A1 Dec. 2, 2021

Related U.S. Application Data

(60) Provisional application No. 62/683,677, filed on Jun. 12, 2018.

(51) Int. Cl.
*H04M 1/66* (2006.01)
*H04W 12/63* (2021.01)
(Continued)

(52) U.S. Cl.
CPC ......... *H04W 12/63* (2021.01); *H04W 12/033* (2021.01); *H04W 12/04* (2013.01); *H04W 12/102* (2021.01)

(58) Field of Classification Search
CPC ..... H04W 12/12; H04W 12/06; H04W 12/63; H04W 12/03; H04W 12/04; H04W 12/02; H04W 12/0431; H04W 12/0471
See application file for complete search history.

(56) References Cited

U.S. PATENT DOCUMENTS

| 5,455,466 A | 10/1995 | Parks et al. |
| 7,155,290 B2 | 12/2006 | Von Arx et al. |

(Continued)

FOREIGN PATENT DOCUMENTS

| CN | 101517940 | 8/2009 |
| CN | 103328041 | 9/2013 |

(Continued)

OTHER PUBLICATIONS

Notification of Office Action and Search Report dated Oct. 9, 2021 From the State Intellectual Property Office of the People's Republic of China Re. Application No. 202080006318.4. (11 Pages).

(Continued)

*Primary Examiner* — Shantell L Heiber

(57) ABSTRACT

Embodiments of communication systems are disclosed for protecting communication between an implanted device ID and an external device ED. For example, a one way Transcutaneous energy transfer TET link may be used to secure two way communication over a radio channel. Optionally, the TET link may be protected from intrusion by a malicious party. For example, the TET link may be over a medium that decays very quickly over distance. In some embodiments, the TET link is used to pass an encryption key and/or to verify communications over the two-way radio channel. The TET channel may be authenticated. For example, authentication may include a minimum energy and/or power transfer.

24 Claims, 10 Drawing Sheets

(51) Int. Cl.
  *H04W 12/033* (2021.01)
  *H04W 12/102* (2021.01)
  *H04W 12/04* (2021.01)

(56) References Cited

U.S. PATENT DOCUMENTS

| | | | |
|---|---|---|---|
| 7,587,241 B2 | 9/2009 | Parramon et al. | |
| 8,214,642 B2 | 7/2012 | Baentsch et al. | |
| 8,254,572 B2 | 8/2012 | Vaughan et al. | |
| 8,331,563 B2 | 12/2012 | Healy et al. | |
| 9,154,002 B2 | 10/2015 | Norconk et al. | |
| 9,401,894 B2 | 7/2016 | Kalpin et al. | |
| 9,763,087 B2 | 12/2017 | Westhues | |
| 2005/0055244 A1* | 3/2005 | Mullan | G16H 40/63 705/2 |
| 2005/0063488 A1 | 3/2005 | Troyk et al. | |
| 2005/0075694 A1 | 4/2005 | Schmeling et al. | |
| 2005/0203582 A1 | 9/2005 | Healy et al. | |
| 2007/0118188 A1 | 5/2007 | Von Arx et al. | |
| 2007/0293142 A1 | 12/2007 | Dehmas et al. | |
| 2007/0293894 A1 | 12/2007 | Zhang et al. | |
| 2008/0288029 A1 | 11/2008 | Healy et al. | |
| 2009/0270949 A1 | 10/2009 | Kalpin et al. | |
| 2010/0076524 A1* | 3/2010 | Forsberg | H02J 7/007192 607/61 |
| 2010/0279606 A1 | 11/2010 | Hillan et al. | |
| 2011/0135092 A1 | 6/2011 | Lehner | |
| 2011/0171905 A1 | 7/2011 | Roberts et al. | |
| 2012/0174187 A1 | 7/2012 | Argon et al. | |
| 2013/0108046 A1 | 5/2013 | Andersen | |
| 2013/0110008 A1* | 5/2013 | Bourget | H04W 12/33 600/595 |
| 2013/0166642 A1* | 6/2013 | Polefko | H04B 7/26 709/204 |
| 2013/0181538 A1* | 7/2013 | Calasso | A61M 5/14276 307/104 |
| 2014/0185805 A1 | 7/2014 | Andersen | |
| 2014/0273824 A1* | 9/2014 | Fenner | A61B 5/0031 455/41.1 |
| 2015/0142653 A1 | 5/2015 | Neumann et al. | |
| 2015/0334563 A1 | 11/2015 | Freda et al. | |
| 2016/0175600 A1* | 6/2016 | Amir | A61N 1/3956 607/59 |
| 2017/0161449 A1 | 6/2017 | Meskens | |
| 2017/0223540 A1 | 8/2017 | Battiwalla et al. | |
| 2018/0036477 A1 | 2/2018 | Olson et al. | |
| 2018/0145838 A1* | 5/2018 | Wang | H04L 9/3278 |
| 2022/0159468 A1 | 5/2022 | Prutchi et al. | |

FOREIGN PATENT DOCUMENTS

| | | |
|---|---|---|
| CN | 104080513 | 10/2014 |
| CN | 106512214 | 3/2017 |
| CN | 106924878 | 7/2017 |
| CN | 107150654 | 9/2017 |
| CN | 107405083 | 11/2017 |
| CN | 108136191 | 6/2018 |
| CN | 109076084 | 12/2018 |
| DE | 102011104364 | 12/2012 |
| WO | WO 99/038272 | 7/1999 |
| WO | WO 2019/239343 | 12/2019 |
| WO | WO 2020/183355 | 9/2020 |

OTHER PUBLICATIONS

International Preliminary Report on Patentability dated Sep. 23, 2021 From the International Bureau of WIPO Re. Application No. PCT/IB2020/052048. (19 Pages).
Notification of Office Action and Search Report dated Mar. 31, 2022 From the State Intellectual Property Office of the People's Republic of China Re. Application No. 201980052087.8. (12 Pages).
Notification of Office Action dated Mar. 18, 2022 From the State Intellectual Property Office of the People's Republic of China Re. Application No. 202080006318.4. (10 Pages).
Notification of Office Action and Search Report dated Sep. 1, 2021 From the State Intellectual Property Office of the People's Republic of China Re. Application No. 201980052087.8 and Its English Summary and Claims. (20 Pages).
International Preliminary Report on Patentability dated Dec. 24, 2020 From the International Bureau of WIPO Re. Application No. PCT/IB2019/054909. (10 Pages).
International Search Report and the Written Opinion dated Nov. 8, 2019 From the International Searching Authority Re. Application No. PCT/IB2019/054909. (17 Pages).
International Search Report and the Written Opinion dated Jul. 27, 2020 From the International Searching Authority Re. Application No. PCT/ IB2020/052048. (25 Pages).
Invitation to Pay Additional Fees, Communication Relating to the Results of the Partial International Search and the Provisional Opinion dated May 15, 2020 From the International Searching Authority Re. Application No. PCT/IB2020/052048. (17 Pages).
Invitation to Pay Additional Fees, Communication Relating to the Results of the Partial International Search and the Provisional Opinion dated Sep. 18, 2019 From the International Searching Authority Re. Application No. PCT/IB2019/054909. (12 Pages).
Bash et al. "Hiding Information in Noise: Fundamental Limits of Covert Wireless Communication", IEEE Communications Magazine, 53(12): 26-31, arXiv:1506.00066vl, May 30, 2015.
Maurer et al. "Unbreakable Keys From Random Noise", Security With Noisy Data, Chap. 1: 21-44, 2007.
Translation Dated Nov. 5, 2021 of Notification of Office Action and Search Report dated Oct. 9, 2021 From the State Intellectual Property Office of the People's Republic of China Re. Application No. 202080006318.4. (6 Pages).
Notification of Office Action and Search Report dated Aug. 29, 2022 From the State Intellectual Property Office of the People's Republic of China Re. Application No. 201980052087.8. (11 Pages).
Translation Dated Apr. 15, 2022 of Notification of Office Action dated Mar. 18, 2022 From the State Intellectual Property Office of the People's Republic of China Re. Application No. 202080006318. 4. (12 Pages).
Translation Dated Jul. 25, 2022 of Decision of Rejection dated Jul. 4, 2022 From the China National Intellectual Property Administration Re. Application No. 202080006318.4. (7 Pages).
Decision of Rejection dated Jul. 24, 2022 From the State Intellectual Property Office of the People's Republic of China Re. Application No. 202080006318.4. (8 Pages).
English Translation Dated Apr. 29, 2022 of Notification of Office Action and Search Report dated Mar. 31, 2022 From the State Intellectual Property Office of the People's Republic of China Re. Application No. 201980052087.8. (13 Pages).
Translation Dated Sep. 13, 2022 of Notification of Office Action dated Aug. 29, 2022 From the China National Intellectual Property Administration Re. Application No. 201980052087.8. (5 Pages).

* cited by examiner

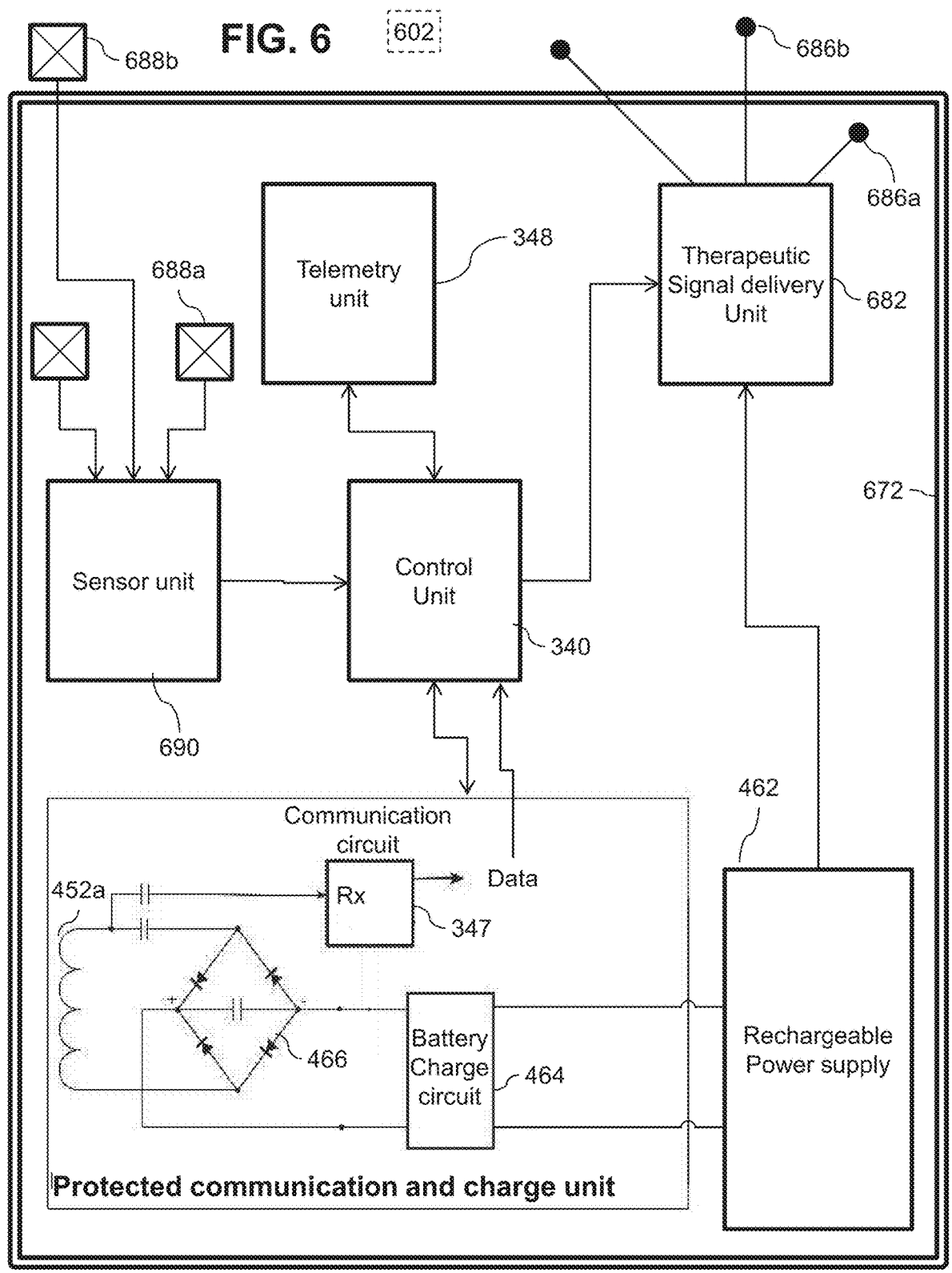

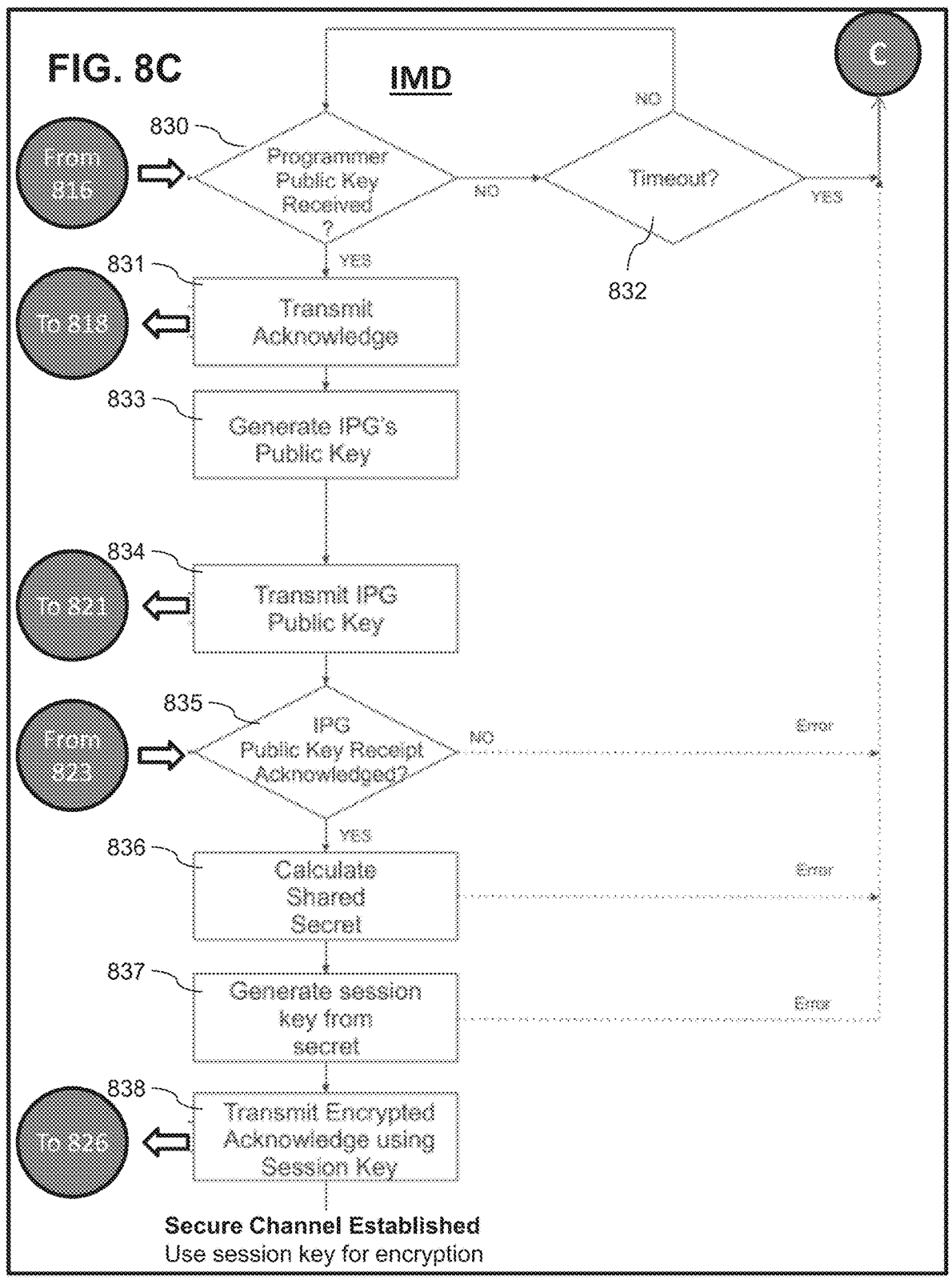

POWER COUPLING MODULATION TRANSMISSION

RELATED APPLICATIONS

This application is a National Phase of PCT Patent Application No. PCT/IB2019/054909 having International filing date of Jun. 12, 2019, which claims the benefit of priority under 35 USC § 119(e) of U.S. Provisional Patent Application No. 62/683,677 filed on Jun. 12, 2018. The contents of the above applications are all incorporated by reference as if fully set forth herein in their entirety.

FIELD AND BACKGROUND OF THE INVENTION

The present invention, in some embodiments thereof, relates to a method of securing wireless communication and, more particularly, but not exclusively, to a method of security key transfer with an implanted medical device over a near field communication channel.

U.S. Published Patent Application no. 20070118188 appears to disclose "A method and system for enabling secure communications between an implantable medical device (IMD) and an external device (ED) over a telemetry channel. A telemetry interlock may be implemented which limits any communications between the ED and the IMD over the telemetry channel, where the telemetry interlock is released when the ED transmits an enable command to the IMD via a short-range communications channel requiring physical proximity to the IMD. As either an alternative or addition to the telemetry interlock, a data communications session between the IMD and ED over the telemetry channel may be allowed to occur only after the IMD and ED have been cryptographically authenticated to one other."

U.S. Published Patent Application no. 20140185805 appears to disclose "Methods and systems for securely exchanging cipher keys between an implantable device and an external device . . . . An example method includes: receiving an authorization request from the external device, wherein the authorization request is a request to receive a first cipher key of a cipher key transfer; receiving an indication that a magnet is detected relative to the implantable device, wherein the indication signifies a secure environment for communication between the implantable device and the external device; and after receiving the authorization request and the indication of a detected magnet, generating a first cipher key transmittal instruction, wherein the first cipher key transmittal instruction instructs the first cipher key to be transmitted to the external device by the implantable device."

U.S. Pat. No. 9,154,002 appears to disclose, "A wireless power supply system that detects communications in the input power to the switching circuit. In this aspect of the invention, the wireless power supply includes a detector for generating a signal indicative of the current in the input to the switching circuitry, a band-pass filter for filtering the detected signal, an amplifier for amplifying the filtered signal, a filter for filtering the amplified signal and a comparator for converting the final signal into a stream of high and low signals that can be passed to a controller for processing as binary data stream. In a second aspect, the wireless power supply system includes a detector for generating a signal that varies in dependence on changes in the phase relationship between the current and the voltage in the primary-side tank circuit, a band-pass filter for filtering the signal, an amplifier for amplifying the filtered signal, a filter for filtering the amplified signal and a comparator for converting the final signal into a stream of high and low signals that can be passed to a controller for processing as binary data stream."

U.S. Pat. No. 5,455,466 appears to disclose, "A system for inductively coupling power and data to a portable electronic device. A portable device, such as a personal digital assistant, is powered or recharged via an inductive coupling between the device and a support unit, thereby eliminating the need for cabling or other connections therebetween. The same inductive coupling is also used to transfer data signals between the device and a second electronic device, for example, a conventional desktop computer. The support unit includes a primary winding of a transformer, a power amplifier and a modulator. The portable device includes a secondary winding connected in parallel with the input of a rectifier, the output of which is connected to a battery charging circuit, and to a modem, which is further connected to the device microprocessor. Placement of the device on the support unit effects the inductive coupling when the primary and secondary windings are in proximity to one another."

SUMMARY OF THE INVENTION

Some examples of some embodiments of the invention are listed below:

Example 1. A method of secure communication between an implanted device and an external device comprising:
transferring energy over a transcutaneous energy transfer (TET) link to an implanted device by the external device;
modulating a verification key onto to said TET link by said external device; and
encrypting communication over a radio channel using said verification key.

Example 2. The method of example 1, wherein the radio channel includes a range at least twice as large as the TET link.

Example 3. The method of any one of examples 1 to 2, wherein the TET link uses at least twice as much power for a transmission as the radio channel.

Example 4. The method of any one of examples 1 to 3, wherein the TET link requires at least twice as time for a transmission as the radio channel.

Example 5. The method of any one of examples 1 to 4, wherein said transferring energy further includes:
inducing a current in an implanted device by the external device.

Example 6. The method of any one of examples 1 to 5, further comprising:
charging a battery of said implanted device with said transferred energy.

Example 7. The method of any of examples 1 to 6, wherein said verification key is a public key and wherein said encrypting includes transmitting a message from said implanted device over said radio channel using asymmetric encryption and said public key.

Example 8. The method of example 7, wherein said message includes a session key, the method further comprising:
encrypting a command to said implanted device with said session key.

Example 9. The method of example 7, wherein said message includes a session key, the method further comprising:
encrypting data sent from said implanted device with said session key.

Example 10. The method of any one of examples 1 to 9, further comprising:

securing a command sent to said implanted device according to a high level security protocol; and securing data sent from said implanted device to an external device according to a low level security protocol.

Example 11. The method of example 10, wherein a command from said external device to said implanted device to change a treatment parameter is assigned said high security level.

Example 12. The method of example 11, wherein said command is temporarily assigned said low security level in response to a condition of a user of the implanted device.

Example 13. The method of example 12, wherein said condition includes a cardiac infarction.

Example 14. The method of any one of examples 10 to 13, wherein said high level security protocol requires modulation of a renewed verification key within 15 minutes before accepting said command.

Example 15. The method of any one of examples 1 to 14, further comprising:

verifying a message sent over said unsecured radio channel by sending a verification message from said external device to the implanted device over said TET link.

Example 16. An implanted device for secure communication comprising:

a transcutaneous energy transfer (TET) receiver configured receiving power from and external device and supplying said power to the implanted device;

a data receiving circuit connected to said TET receiver configured to receive a public key from said TET receiver;

an encryption module functionally connected to said data receiving circuit for receiving said public key from said data receiving circuit and configured for encrypting a message with asymmetric encryption based on said public key to produce an encrypted message, and a transceiver functionally connected to receive said encrypted message from said transceiver and send said encrypted message to said external device over a two way radio channel.

Example 17. The device of example 16, wherein the implanted device does not include a modulator capable of modulating an outgoing message onto said TET channel.

Example 18. The device of any one of example 16 to 17, wherein the implanted device does not include an asymmetric decryption circuit capable of generating said public key and a private key and decrypting an asymmetric encrypted message encrypted with said public key.

Example 19. The device of any one of examples 16 to 18, further comprising a rechargeable power supply for said implanted device, said power supply functionally attached to said TET receiver for recharging from said power supplied by said external device.

Example 20. The device of any one of examples 16 to 19, wherein said external device includes a TET generator configured to transmit energy to the implanted device and an asymmetric decryption circuit capable of generating said public key and a private key and decrypting an asymmetric encrypted message encrypted with said public key and a modulator functionally connected to said decryption circuit for receiving said public key and said modulator functionally connected to said TET generator for modulating said public key onto a TET signal and transferring said key to the implanted device.

Example 21. The device of example 20, wherein said external device does not include a receiver capable of receiving a message over said TET channel.

Example 22. A method of managing security of an implanted device comprising:

detecting a current location;

adjusting a security protocol according to said current location.

Example 23. The method of example 22, wherein said location is a high risk location and said adjusting includes increasing security limitations.

Example 24. The method of any one of examples 22 to 23, wherein said location is a low risk location and said adjusting includes decreasing security limitations.

Example 25. A system to perform the method of any one of examples 22 to 24.

Example 26. A method of managing security of an implanted device comprising:

detecting a current condition of a user of the device;

adjusting a security protocol according to said current condition.

Example 27. The method of example 26, wherein said condition is stable and said adjusting includes increasing security limitations.

Example 28. The method of any one of examples 26 to 27, wherein said condition includes an acutely dangerous condition and adjusting includes decreasing security limitations.

Example 29. A system to perform the method of any one of examples 26 to 28.

Example 30. A system for secure communication between an implanted device and an external device comprising:

an implanted device including;

an inductive energy receiving circuit;

a data receiving circuit capable of demodulating a signal from said energy receiving circuit;

a transceiver for data communication over a radio channel; and a processor configured for:

encrypting a message with an asymmetric protocol;

generating a symmetric encryption key;

encrypting data using a said symmetric encryption key to produce an encrypted signal decrypting a received data signal using said symmetric encryption key; and a near field external device including, an induction generating circuit configured for inducting a current on said inducting energy receiving circuit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as an integrated circuit (for example a chip). As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 is a block diagram of an implanted medical device in accordance with an embodiment of the current invention; FIGS. 8A-C are schematic diagrams illustrating security modes in accordance with an embodiment of the current invention.

DESCRIPTION OF SPECIFIC EMBODIMENTS OF THE INVENTION

Figure 1:
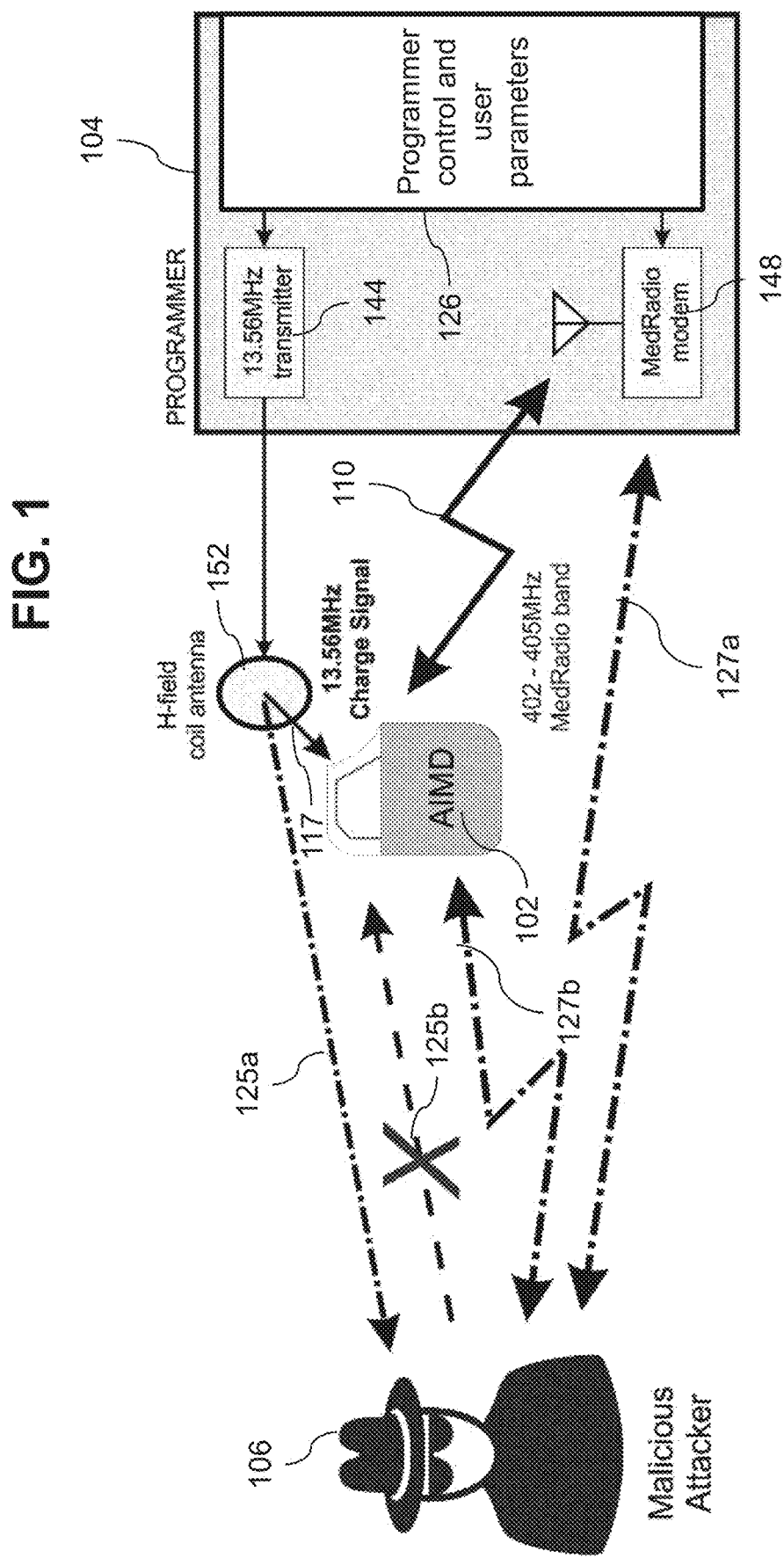
FIG. 1 is a schematic block diagram of a system and method of communication with an implanted device in accordance with an embodiment of the current invention.

The present invention, in some embodiments thereof, relates to a method of securing wireless communication and, more particularly, but not exclusively, to a method of security key transfer with an implanted medical device over a near field communication channel.

Overview

An aspect of some embodiments of the current invention relates to a security protocol for leveraging a one way intrusion resistant channel to secure communication between an implanted medical device and an external device on a less secure channel. In some embodiments, the secure channel will include a transcutaneous energy transfer (TET) link (for example including an inductive coupling). For example the TET link may be secured to prevent intrusion (for example preventing an unauthorized party from transmitting fraudulent communications on the channel). Optionally, a security key will be transferred over the intrusion resistant channel. For example, the security key may be used to secure information transferred over a separate channel, for example a one and/or two way radio channel. Optionally, there will be different levels of security on the key transfer and/or the key itself (how strong is the key) that are required for different communications.

In some embodiments, different levels of security will apply for different types of messages, different locations, different times and/or under different conditions (for example when a dangerous medical condition is detected the device may allow short term reprogramming that it would not allow under normal conditions). Optionally, some communications over the unprotected channel will only be implemented after confirmation over the intrusion resistant channel.

In some embodiments, the IMD may require authentication before receiving an encryption key. Optionally the authentication may be data based and/or non-data based. For example, the authentication may require functions that would be difficult to replicate by an intruder device. For example, a powerful transmitter may be required to be located very close to IMD. For example, transfer of the security may be initiated only when the IMD receives a sufficient quantity of energy and/or sufficient power and/or for a sufficient time over a TET channel. Alternatively or additionally, the security key transfer may only be initiated according to instructions passed over a separate channel. For example, initiation of a key transfer may require a command and/or a key passed to the IMD through a different channel. For example, the timing of the key transfer may be limited to a time transmitted over the two way data channel. Alternatively or additionally, the key transfer by require the ED to specify a session sequence from a communication over another channel. Optionally, an IMD may include a location detection device (e.g. a GPS) and/or may only accept a security key in a predetermined location.

In some embodiments, an asymmetric public key is optionally sent from the ED to the IMD over the intrusion resistant channel. The asymmetric key is optionally used for encrypted communication over another non-safe second channel. Asymmetric encryption may be used to send a session key from the IMD to the ED and/or the session key may be used for further communication. For example, the security key may be used to encrypt data and/or commands being sent over a MedRadio [MICS] channel. Optionally, the intrusion resistant channel may include a very short range channel (for example based on inductive coupling). In some embodiments the IMD may not be capable of generating a pair of keys for asymmetric communication keys. In some embodiments the IMD may not be capable of using a private key to decrypt a message encrypted with an asymmetric public key. For example, the processor of the IMD may be too weak for asymmetric decryption and/or may lack software instructions for asymmetric decryption.

In some cases, for example, when the IMD detects an emergency medical situation, certain communications may be allowed with an abbreviated security protocol. Optionally, some functions may be controlled only so long as an inductive device is in communication with the IMD. In some embodiments, certain functions may require security clearance including a security key passed over the protected channel.

In some embodiments, an IMD may have various security states and/or have functions that require different security levels. For example, to change life affecting settings of the IMD may require high security clearance, for example by use of a fresh security key and/or a key received over a protected channel. Alternatively or additionally, the ED receiving data from the IMD may be possible using an older security key. Alternatively or additionally, the IMD may have an emergency mode which allows changing of important (and/or life affecting) parameters with a lower security for a limited time. Alternatively or additionally, the security requirements for certain actions may be adjustable by a user having a sufficient security level. Optionally, an ED may have security protection such as a password and/or a biometric identifier to prevent unauthorized access. Alternatively or additionally, some aspects of the ED may require less or no security (for example charging a battery of the IMD) while other functions (for example viewing data) may need require medium level security (for example supplying a password) while other functions (for example reprogramming the IMD) may require high level security (for example biometric identification and/or a strong password).

For example, the ED may include a secure channel (for example a TET link) and/or a non-secure channel (for example a radio channel). A secure channel optionally includes a characteristic which makes it difficult for a hidden device to receive and/or transmit a signal. For example, the secure channel may be intrusion resistant. For example, an intrusion resistant channel may include a very short range communication medium (for example inductive coupling). For example the range of the secure channel may be less than $\frac{1}{2}$ and/or less than $\frac{1}{5}$ and/or less than $\frac{1}{10}$ and/or less than $\frac{1}{20}$ of the range of the non-secure channel. In some embodiments, an intrusion resistant channel may require high levels of power to transfer a signal. For example, the IMD may require transfer of enough power to charge a battery of the IMD before accepting a signal over the secure channel. For example transferring a message over the secure channel may require more than twice the energy and more than 5 times and/or more than 10 times and/or more than 20 times the energy for transferring the signal over the non-secure channel. In some embodiments communication may require a large time. For example, the IMD may require long contact time before accepting communication over the secure channel. For example transferring a message over the secure channel require more than twice the time and more than 20 times and/or more than 100 times and/or more than 1000 times the time for transferring the signal over the non-secure channel.

In the some embodiments, the ED will include security features to prevent misuse of the device. For example, the features may be activated to prevent unauthorized use of the ED for reprograming of the IMD. For example, the ED may include a biometric identification system. Optionally, the ED is programmed to change certain parameters of the ED only after positive identification and/or approval of a local user and/or approval of a supervisor (e.g. a doctor and/or a control center). In some embodiments, actions of the ED and/or the IMD are logged and/or data is sent to a control center. For example the logs may be checked manually and/or automatically to detect unusual activity and/or potentially dangerous situations.

An aspect of some embodiments of the current invention relates to a system for protecting communication between an IMD and an ED using infiltration resistant Transcutaneous Energy Transfer (TET) link. For example, the TET link may be configured for one way energy transfer from the ED to a battery on the IMD and/or one way communication from the ED to the IMD. In some embodiments, the system includes a two way radio link between the IMD and the ED. Optionally, the ED includes a processor configured for asymmetric key generating and decryption and/or the IMD includes a processor configured for asymmetric encryption based on a public key. For example, the public key may be supplied to the IMD over the TET link. Optionally, the ED includes a processor configured for symmetric key generating and encryption/decryption. Alternatively or additionally a key may be supplied to the ED from an external source (for example a network and/or an electronic data storage device).

In some embodiments, the IMD lacks circuitry and/or software to modulate a data signal onto the TET channel. Optionally, the ED lacks circuitry or software to receive a data signal over the TET channel.

In some embodiments, an IMD may include a therapeutic device for example a pacemaker and/or an implantable defibrillator, a neurostimulator, a cochlear implant, a gastric stimulator, a pump (e.g. an insulin pump), a foot drop implant, and/or a cardiac contractility modulation CCM device. Alternatively an implanted device may include a sensor.

An aspect of some embodiments of the current invention relates to an implanted device that adjusts its security according to a condition of a subject. For example, for a subject in a healthy state, the device may employ high level security protocols to protect data and/or prevent tampering with device functions. Alternatively or additionally, the device may accept commands and/or transfer data with lower security protocols at particular times and/or under certain conditions. For example, security may be reduced when there is an emergency medical condition that may require emergency and/or lifesaving intervention. For example, the device may include a sensor that senses a medical state of a subject and/or a processor that interprets sensor data and/or controls security.

An aspect of some embodiments of the current invention relates to an implanted device that adjusts its security according to a location. For example, in certain predetermined locations the device may reduce security requirements (for example security limitations may be reduced in a low risk location, for example in the home of the subject and/or security limitations may be reduced in a location where therapeutic interventions are expected, for example an emergency room and/or in a doctor's office). Alternatively or additionally, in certain locations the device may increase its security for example, in a foreign country and/or near an embassy of a hostile country and/or in a high crime area. In some embodiments, the implanted device may include a location sensor (for example a GPS) and/or security may be adjusted according to the location. Alternatively or additionally, certain locations (for example a doctor's office and/or an emergency room) may have location indicator devices that are detected by the IMD.

EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a schematic view of a system and method of securing communication between an implanted medical device (IMD) 102 and an external device (ED)104 from infiltration by an intruder 106. In some embodiments, IMD 102 communicates with ED 104 over multiple wireless media. For example a one way intrusion resistant medium 117 may be used for communication from the ED 104 to the IMD 102. For example, the ED 104 may include a transmitter 144 configured for one way transmission to the IMD which may include a receiver for receiving signals over the intrusion resistant channel. Optionally the intrusion resistant channel includes a TET link. In some embodiments the length of transmission on the intrusion resistant channel may be limited, for example to between 1 to 5 cm and/or between 5 to 15 cm and/or between 15 to 100 cm. For example, a non-secure medium 110 may be used for two way communication. For example, the ED 104 and/or IMD 102 may include a radio transceiver 148. For example, receiver 148 may be configured for two way communication over a MedRadio band (e.g. between 402 to 405 MHz). In some embodiments the length of these transmissions may be limited, for example to between 1 to 3 meters and/or between 3 to 30 m and/or between 30 to 100 meters and/or between 100 to 1000 meters.

In some embodiments, signals from the ED 104 to the IMD 102 may include control commands and/or performance parameters 126 for the IMD 102. Parameters 126 are optionally stored in the ED 104. For example, in a computer accessible memory and/or received from a remote source and/or from a local programmer and/or generated by a local and/or remote processor. For example, operating parameters of the IMD 102 may be adjusted according to data received from the ED 104. In some embodiments the IMD may include a read/write computer readable member for storing alternative parameter values and/or a clock (for example a real time clock). For example, the IMD may receive a temporary set of parameters from the ED. The IMD may then store a current set of parameters in the computer readable memory and/or the IMD may use the temporary parameters for a predetermined period and reinstate the previous parameters after the period.

In some embodiments, the intrusion resistant medium 117 may be protected from infiltration 125b. Nevertheless, in some embodiments, the intrusion resistant medium 117 may be vulnerable to interception 125a. For example intrusion resistant medium 117 may include a TET link. The TET link may be used to charge a power supply (for example a battery) of the IMD. For example, the inductive coupling may be used for the power transfer. Additionally or alternatively, the ED 104 may transmit signals to the IMD 102 over channel 117. For example, the ED may include a transmitter 144 to transmit signals over the TET link at carrier frequency between 12-14 MHz or more or less. Optionally the TET link between the ED 104 and the IMD 102 may be limited in range for example to less than 5 cm and/or less than 10 cm and/or less than 30 cm and/or less than 1 m.

In some embodiments, the currently-disclosed invention is configured to secure communication under the assumption that communications between the IMD 102 and external device 104 on the intrusion resistance medium 117 can be conceivably received 125a by a malicious eavesdropper 106 (for example with sufficiently sensitive receivers). The malicious attacker 106 could conceivably transmit 127a, 127b signals via MedRadio that can be received by the ED 104 and/or the IMD 102 at a distance. Nevertheless, the system is optionally configured to inhibit attacker 106 from controlling the IMD 102. For example, the attacker may be prevented from transmitting a spoofed message 125b to the IMD 102 over the intrusion resistant medium 117. For example, to make such a transmission may require an unreasonably large H-field transmitter and/or approaching unreasonably close to the IMD 102. For example the system prevents the attacker 106 from spoofing a programmer-to-IPG communication over the intrusion resistant channel 117 without being detected. For example, in some embodiments, a security protocol may amplify the limitations of the attacker 106. For example, a security protocol may require a predetermined signal power and/or energy transfer before accepting an encryption key over the intrusion resistant channel 117. For example, it may be difficult for a malicious attacker 106 to acquire that much power and/or transfer that much power to the IMD 102 when his device is hidden (for example requiring only a small power source and/or preventing connection to a fixed power cable).

Figure 4:
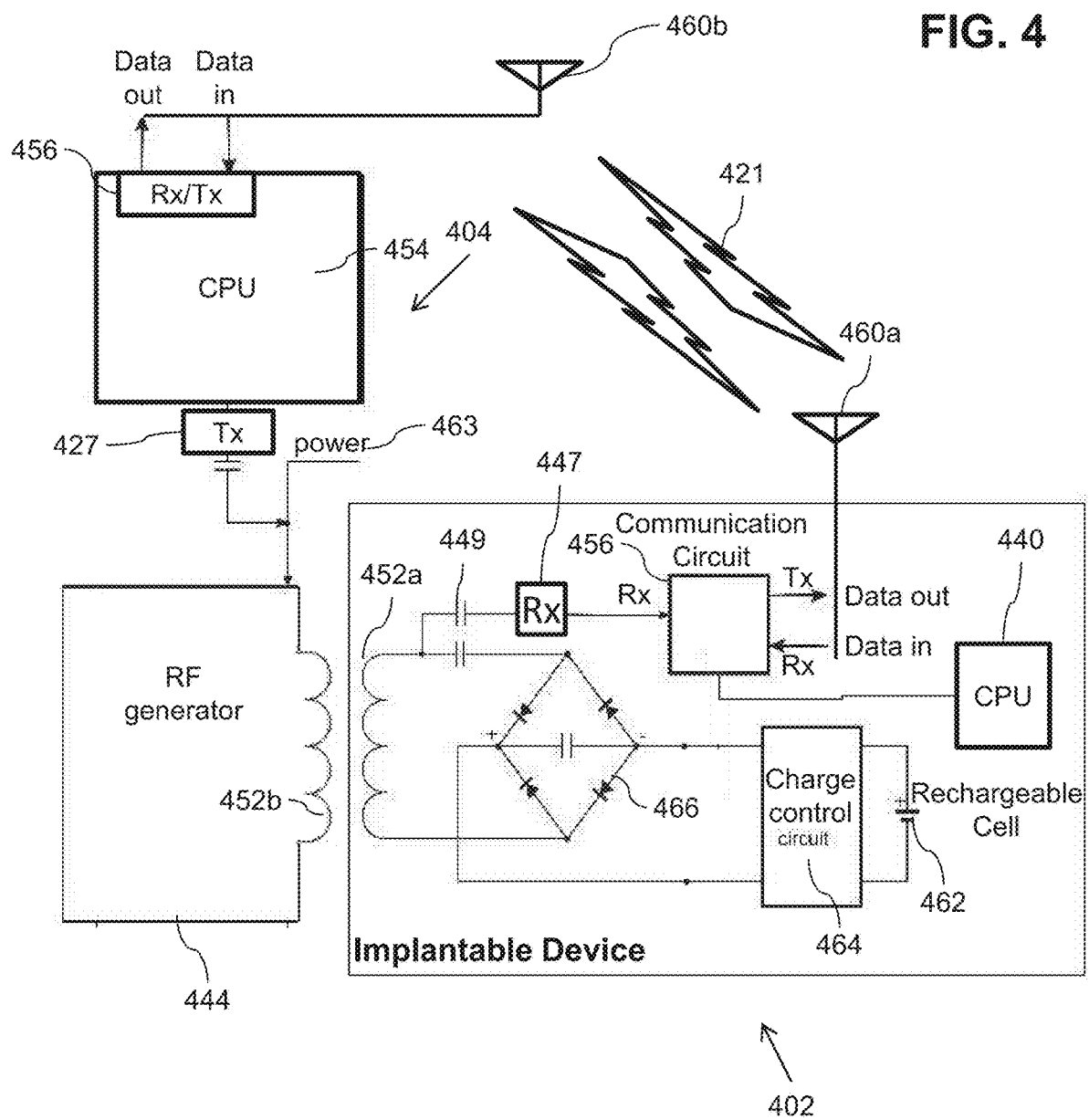
FIG. 4 is a circuit diagram of system for communicating in accordance with an embodiment of the current invention.

In some embodiments, the coupling on the intrusion resistant channel decays very rapidly with distance between the transmitter (e.g. a coil 152 in the ED) and the receiver (e.g. internal coil for example as illustrated by coil 452a of FIG. 4) used to receive the transcutaneously-transmitted energy. For example, the recharge distance 104 between the external charger coil and the implant may be restricted to just a few centimeters (e.g. <5 cm). As such, a malicious attacker 106 attempting to transmit data over the recharge channel to an AIMD over a larger distance would require a very large and powerful transmitter and antenna. The need to operate a large transmitter in the vicinity of the IMD may inhibit a surreptitious attack.

In some embodiments, transferring a key and/or verification for security communications at some predetermined level will be limited by time and/or location. For example, an IMD 102 may include a location determination circuit (for example a GPS receiver). The IMD 102 optionally only accepts passwords in a known protected location (for example in the house of the user and/or in one or more known locations for example a hospital and/or an office of a trusted practitioner). For example, this may prevent an attacker 106 from inviting a user of the IMD 102 to a location where attacker has a hidden transmitter with enough power to intrude into the system and/or spoof communications to the IMD 102 over channel 117. In some embodiments, the IMD 102 may accept a key at some predetermined security level at specific times. For example, this may prevent an attacker 106 from sneaking up on a user of IMD 104 at an unexpected moment (for example while he is sleeping). In some embodiments, acceptance of a key at a certain security level by the IMD 102 will depend on a physiological state of the user of the IMD 102. For example, the IMD 102 may not accept a key for changing a long term treatment parameter of the device while the user is asleep. For example, when the IMD 102 detects an emergency condition (for example a cardiac infarction, the IMD 102 may allow emergency short term changes in functioning parameters with abbreviated security protocol.

In some embodiments, performance of certain function by the IMD 102 may be dependent on the link to the ED 104. Optionally, functions that are highly security sensitive and/or require high power may be performed only under certain circumstance including for example while the IMD 102 is receiving power from the ED 104 over the TET link. For example, communication of a session key using asymmetric encryption may be performed only under certain conditions including for example when the IMD 102 is receiving power on the TET link and/or when the battery power of the IMD 102 is at some minimum capacity.

Figure 2:
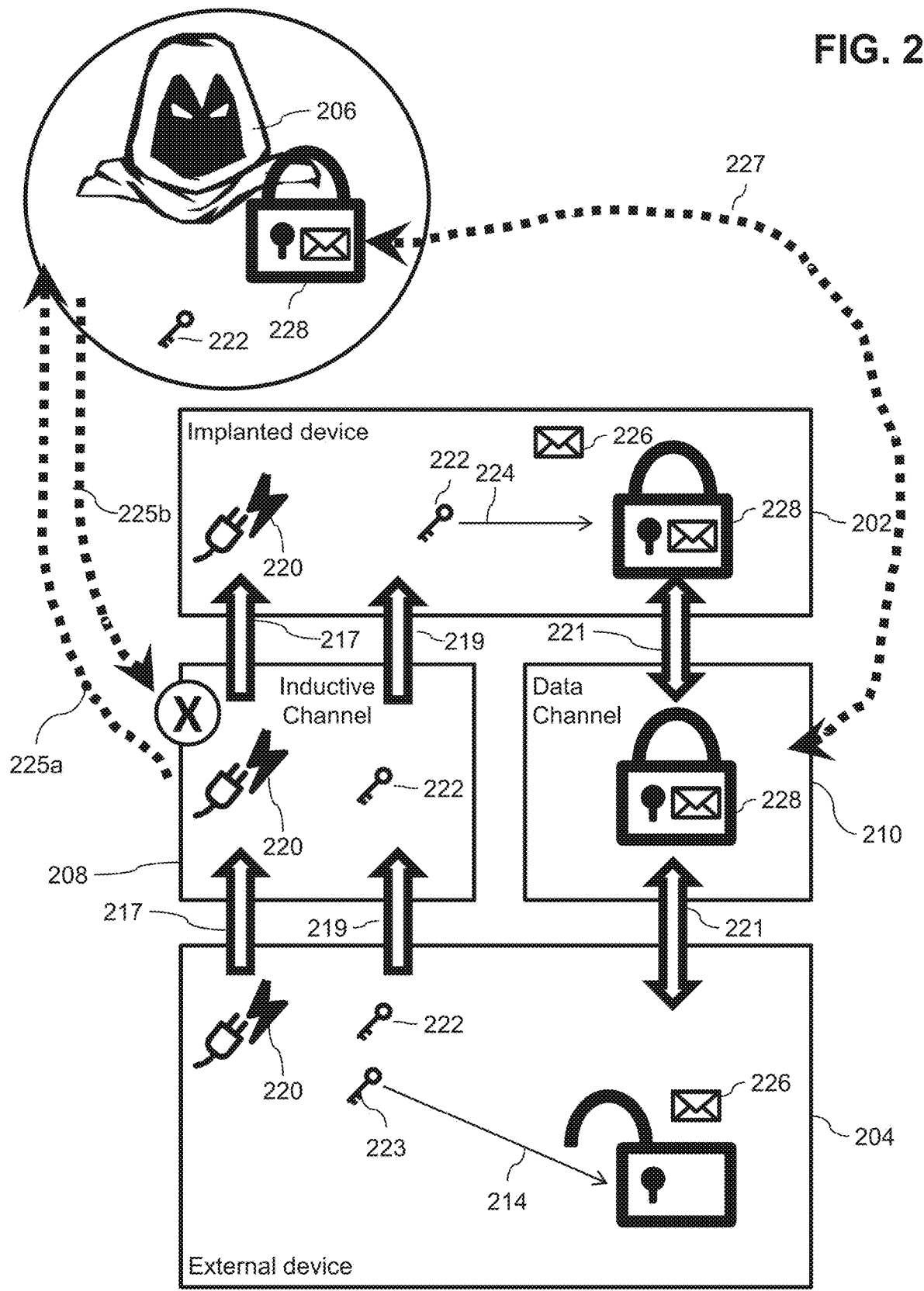
FIG. 2 is a schematic block diagram of a system and method of communicating in accordance with an embodiment of the current invention.

FIG. 2 is a schematic block diagram of a system and method of communicating in accordance with an embodiment of the current invention. In some embodiments, a protected communication process will include a transfer (for example a cryptographic key-transfer 219) between the IMD and a valid external device (e.g. ED 204). This transfer may be made, for example, over the short-range channel 208 implemented over the TET (Transcutaneous energy transfer) link. Optionally the TET is used for to supply energy and/or to recharge 217 the IMD 202. The transfer step is optionally designed to exploit the asymmetry between the valid ED 204 and the malicious intruder 206 to transmit data and/or energy 220 that can be received by the IMD 202. For example, communication over the "long-range" channel is secured when the malicious attacker 206 is not able to "spoof" 225b the transmission of data from the valid ED 204 to the IMD 202. Optionally, the security system is designed such that interception 225a of the data transmitted over the intrusion resistant link 208 shall not give a malicious attacker the means to compromise the security of the long-distance communication 221.

In some embodiments, the availability of a known intrusion resistant short range communication link 208 is leveraged to securely encrypt communications over an unprotected channel 210 (for example, a MedRadio channel). For example, the intrusion resistant channel 208 is used to transfer an asymmetric public key 222. For example the length of the asymmetric encryption public key 222 and/or private key 223 may range for example between 32 bits and 256 bits. Optionally, the system may use asymmetric (public key) cryptography 228 for the ED 204 and the IMD 102 to agree on a session encryption key. For example, the IMD may generate a session key and/or send the session key in a message 226 to the ED 204. For example message 226 may encrypted 224 by IMD 202 using public key 222 and/or transmitted in an encrypted message 228, but not transmitted unencrypted over either channel 208, 210. Encryption with the asymmetric key inhibits the attacker from communicating 225b, 227 with the IPG even if the short range communication is intercepted 225a. The ED 204 may receive the encrypted message 228 over the data channel 210 and/or decrypt 214 the data 226 (including for example the session key) using its private key 222. Optionally private key 223 was never transmitted over any channel (for example over either channel 208 and/or 210). For example, the private key 223 may be generated by and remains local to the ED 204.

In some embodiments, two-way communication between the ED 204 and the IMD 206 is encrypted/decrypted with the session key. Optionally the session key may include for example between 32 to 256 key bits plus a number of auxiliary protocol bits. The session key may only be valid for a predefined short period of time (for example less than one minute and/or between 1 to 5 minutes and/or between 5 minutes to 30 minutes and/or between 30 minutes to 6 hours and/or between 6 hours to 48 hours and/or between 48 hours to a week and/or between a week and a month. Alternatively or additionally, for low security data, a session key may be used continuously between charging session of the IMD 202. Renewing the session key periodically may prevent the use of brute force attacks or statistical methods to attack the MedRadio link. Optionally multiple session keys may be used simultaneously and/or after a certain period of time an old session key may be used for only low security data, but high security will require a renewed session key. In some embodiments, multiple session keys will be transferred in a charging session and/or switched between charging sessions. This strategy has the added benefit that the computational (and therefore power) demands placed on the IMD 202 to do the encryption are reasonably able to be implemented in a microcontroller. Optionally, of the more computationally intensive cryptographic processes are performed on the ED 204, which will be built around a more powerful processor with less stringent energy limitations. This procedure allows communications between the IMD 202 and ED 204 to proceed over the MedRadio link while protecting the system from an attacker 206 remotely reprogramming the IMD 202.

In some embodiments, even if an attacker 206 intercepts communication on one or both of the protected channel 208 and/or the two-way data channel 210, he will be left with an asymmetric public encryption key 222 and/or encrypted data 228 but the attacker will be prevented from acquiring a decryption key (either the asymmetric decryption key 223 and/or a symmetric key that was transmitted in an encrypted form). Alternatively or additionally, communication 219 in the intrusion proof channel 208 may include verification of commands to the IMD 202. For example, even if the attacker 206 is capable of spoofing a malicious command over the data channel 210 to command the IMD 202, the IMD 202 will not carry out the command until it receives verification transmitted 219 by the legitimate ED 202 over the intrusion resistant channel 208. Optionally verification may include a specific data for example repeating a parameter value which the IMD 202 is to implement. Optionally, when a suspicious incident occurs (for example a command is received but not verified), a warning message is transmitted by the IMD 202 to the ED 104 and/or to a security center.

In some embodiments, a system leverages an intrusion resistant channel 208 (for example a TET link) to secure communication between an IMD 202 and an ED 204 over another channel 210. Optionally, the intrusion resistant channel may include an inductive coupling which may be used for intrusion resistant communication 219 and/or power transfer 217. For example the power transfer 217 and/or communication 219 may be one-way (for example from the ED 204 to the IMD 202). For example the power transfer may be at a rate ranging between 0.1 to 0.3 Watts and/or 0.3 to 1 Watt and/or 1 Watt to 5 Watts. Data rate of transmission over the TET channel may range for example between 50 to 200 bits/s and/or 200 to 1 Kbit/s and/or between 1 Kbit/s to 5 Kbit/s and/or between 5 Kbits/s to 20 Kbits/sec. A second communication channel 210 optionally supports two-way communication. For example the data transmission rate on the two-way communication channel 210 may range between 1 kbit/s to 100 Kbit/s and/or between 100 Kbit/sec and/or from 100 Kbit/s to 1 Mbit/s and/or between 1 to 5 Mbit/sec and/or between 5 to 25 Mbits/s. Optionally the carrier frequency of the communication channel may range between 402 to 405 and 433 to 435 MHz and/or between 2.4 GHz to 2.5 GHz. In some embodiments, the ED 204 may charge the IMD 202 with between 0.1 to 0.5 Watt hours and/or 0.5 to 1 Watt hour and/or between 0.5 to 10 Watt Hours of energy in a single session.

Figure 3:
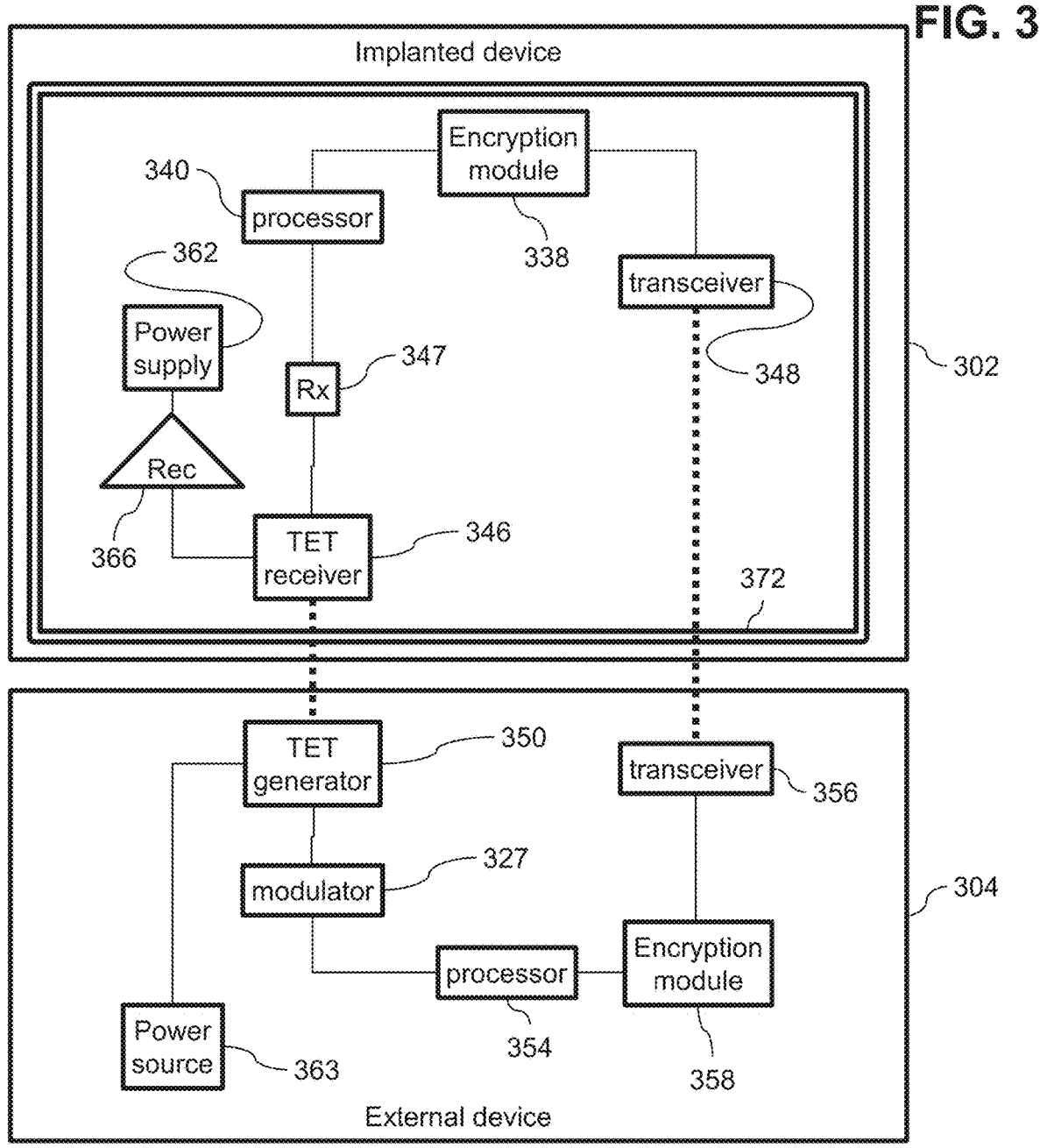
FIG. 3 is a block diagram of system for communicating in accordance with an embodiment of the current invention.

FIG. 3 is a block diagram of system for communicating in accordance with an embodiment of the current invention. In some embodiments an IMD 302 includes two communication modules. Optionally, a first communication module includes a signal receiver 347 connected to a TET receiver 346 for one way communication over TET channel (for example an inductive coupling). Optionally, a second communication module includes a transceiver 348 for two way communication, for example on a radio (e.g. radio wave and/or microwave) channel. For example, transceiver 348 may communicate with a transceiver 356 on the ED 304. Optionally the TET receiver is also connected to a power supply 362 (for example including a rechargeable battery), for example via a rectifying circuit 366. Optionally, IMD 302 is in communication with an ED 304. For example the ED 304 may include a TET generator 350. Optionally, TET generator 350 is connected to a power source 363. Optionally, energy produced power source 363 is transferred by TET generator 350 to TET receiver 346 and/or rectified by rectifier circuit 366 and/or supplied to recharge power supply 362. In some embodiments, ED 304 includes a modulator 327 connected to TET generator 350. For example, a signal from modulator 327 may be transmitted via TET generator 350 over the TET coupling to TET receiver 346. Optionally, the signal is picked up by signal receiver 347.

In some embodiments, TET 350 is positioned outside a body of a patient at close range to TET receiver 346 which may be positioned inside the patient. For example, the distance between TET generator 350 and TET receiver 346 may range between 0 to 1 cm and/or between 1 to 2 cm and/or between 2 to 5 cm and/or between 5 to 8 cm and/or between 8 to 12 cm and/or between 12 to 20 cm.

In some embodiments, TET generator 350 and receiver 346 may include inductive coils. Optionally, receiver 347 may include a band pass filter and/or a modem and/or an amplifier and/or an analogue to digital converter and/or a universal asynchronous transmitter and receiver (UART). For example, rectifier circuit 366 may include a bridge rectifier circuit.

In some embodiments, IMD 302 may be encased in a biocompatible and/or water resistant casing 372.

In some embodiments, an IMD 302 may include a processor 340. Processor 340 optionally includes an encryption module 338. Optionally encryption/decryption/key generation could be in either hardware, software, or a combination (i.e. software with hardware acceleration). For example module 338 may include programs stored in a computer readable memory to support transmitting asymmetrically encrypted data using a public key. Alternatively or additionally, encryption module 338 may include dedicated circuitry and/or a dedicated processor. Processor 340 and/or module 338 are optionally, capable of symmetric encoding and/or decoding of data. For example, processor 340 and/or module 338 may be capable of supporting encrypted communication at rate of between 0.1 to 0.5 Mbps and/or between 0.5 to 5 Mbps and/or between 5 to 20 Mbps and/or between 20 to 100 Mbps and/or generating encryption keys. Optionally, processor 340 and/or module 338 may be capable of communicating and processing messages encrypted with for example between 32 to 256 key bits plus a number or auxiliary protocol bits. Optionally the IMD 202 includes a recharge circuit capable of recharging the power storage in a time ranging between 10 minutest to 30 minutes and/or 30 minutes to 1 hour and/or between 1 to 4 hours. Processor 340 optionally is connected to and/or receives signals (which may optionally be digitized) from receiver 347.

Processor 340 and/or module 338 optionally are connected to and/or send and/or receive signals through receiver 348.

In some embodiments, the ED 304 may include a processor 354 and/or an encryption module 358 capable of decoding asymmetrically encoded communication for example encrypted with between 32 to 256 key bits and/or generating asymmetric encryption keys. Alternatively or additionally, the ED 304 may be capable of protected communication of passwords and/or asymmetrically encoded data with an external processor. For example communication may be over a protected medium (e.g. a hard wired link and/or by means of a data storage device (for example a USB drive). Optionally the power source 363 receives power from an external network for example an electrical power grid. Alternatively or additionally, the power source 363 may include a local power supply, for example a rechargeable cell with a capacity ranging 0.1 to 1.0 Watt hours and/or between 1.0 to 3 Watt hours and/or between 3 to 10 Watt hours and/or a single use cell with a capacity ranging 0.5 to 1.0 Watt hours and/or between 1.0 to 3 Watt hours and/or between 3 to 10 Watt hours and/or between 10 to 30 Watt hours.

FIG. 4 is a circuit diagram of system for communicating in accordance with an embodiment of the current invention. In some embodiments, coil 452b of an ED 404 receives power from a power source 463 and/or a one-way outgoing signal from an RF generator 444. The power is optionally transferred over a TET link to the IMD 402. For example, the TET link may transfer power and/or data inductively to an inductance coil 452a of an IMD 402. Optionally, coil 452a is connected via a rectifying circuit 466 (for example a full bridge rectifier as depicted in FIG. 4) to a charge control circuit 464 and/or a rechargeable power source 462. Alternatively or additionally, coil 452a is connected to a signal receiver circuit 447 which demodulates a one-way incoming signal. For example, circuit 447 may be connected to coil 452a via a tuned capacitor and/or band pass filter 449. Data from circuit 447 is sent over a one-way link to a communication module 456. Module 456 is optionally configured for sending asymmetric encryption of outgoing signals over a radio transceiver 460a. For example, outgoing asymmetrically encoding signals may be encoded using a public key received from receiver 447 and/or from the TET inductance channel from an ED. Module 456 is optionally configured for symmetric decryption and/or encryption of signals over a two way radio channel 421. Optionally, transceiver 460a includes a dedicated antenna. Alternatively or additionally, transceiver 460a uses coil 452a as a radio antenna. Communication is optionally controlled by a controller 440. Optionally communication circuit 456 and/or controller 440 includes a memory for storing an asymmetric key received over the TET link.

In some embodiments, an ED 404 includes a two way transceiver 460b for communicating of radio channel 421 with IMD 402. Optionally, ED 404 includes a processor 454. For example, processor 454 may be configured for asymmetric and/or symmetric encoding and/or decoding and/or for generating of keys for symmetric and/or asymmetric encryption/decryption. For example, processor 454 is connected to a module 427 for one-way encoding of an asymmetric public key and transfer of the public key to RF generator and/or over the TET link to IMD 402. In some embodiments, at some times when asymmetric communication is not being used an asymmetric encoding module 456 and/or processor 440 may be shut down. For example, an asymmetric encoding module may be shut down when IMD 502 is not receiving power over the TET link. For example shutting down an asymmetric encryption module may save power.

Figure 5A:
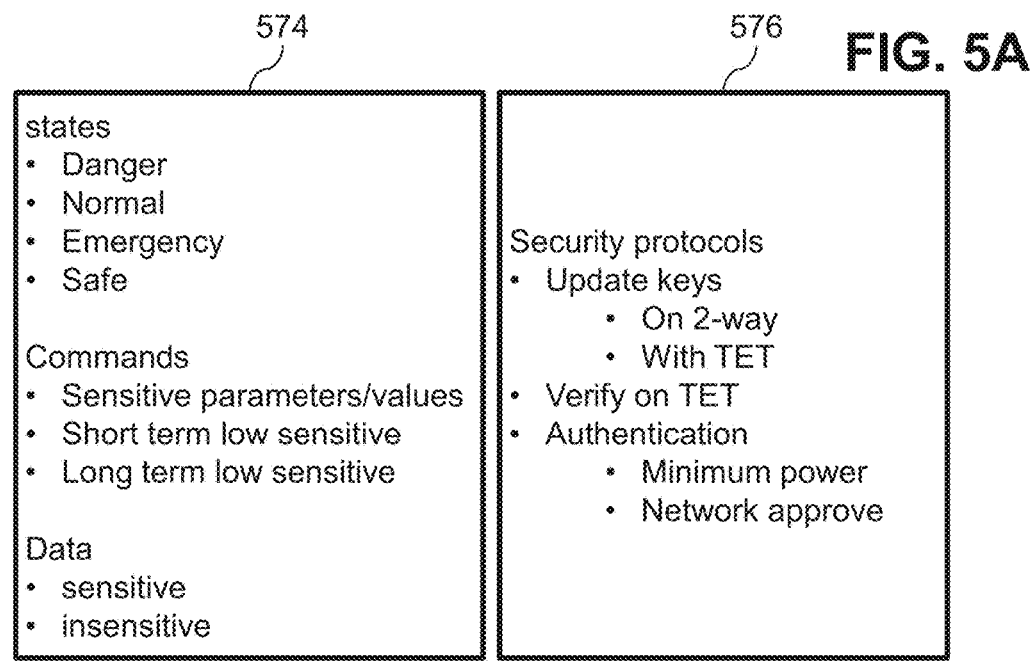
FIGS. 5A and 5B are schematic diagrams illustrating signal flow and/or security protocols in accordance with an embodiment of the current invention.

FIG. 5A is a schematic diagram illustrating signal flow and/or security protocols in accordance with an embodiment of the current invention. Various contents of communications and/or security states 574 may be protected by various security protocols 576 for example in accordance with a sensitivity and/or urgency of the communication.

In some embodiments, an IMD may have various security states. For example, the IMD may recognize a state in which there is an increased risk of malicious attack. For example, there may be an increased risk of malicious attack when the device (and/or the person to which the device is implanted) is in an unsecured location, for example where a malicious attacker may be able to position malicious hardware. For example, there may be an increased risk of malicious attack when the person in whom the device is implanted is asleep and/or at night when the user may be unaware of malicious hardware being positioned next to his body. Optionally, the IMD 568 may include positioning indicator (for example a GPS receiver and or a list of stored locations that are safe and/or unsafe) and/or a sensor to determine a state of the user (e.g. asleep, awake by a pulse sensor and/or a blood pressure sensor). For example, in a state with increased risk of attack, a device may not allow certain sensitive communications (for example a command that would shut down a lifesaving system and/or change a parameter of functioning of the IMD 502 that could endanger the user of the device and/or a permanent parameter changes). Alternatively or additionally, in a state where there is increased risk the IMD 502 may require increased security protocols and/or verification over a normal mode.

In some embodiments, an IMD 502 may have a normal mode. For example, in the normal mode, certain changes and/or communications may be allowed and/or other changes may be prohibited. Alternatively or additionally, certain security protocols may be in place to protect the data and/or commands from malicious attack.

In some embodiments an IMD 502 may have an emergency mode. For example, when an IMD 502 detects a symptom of a dangerous health condition (for example a myocardial infarction and/or an ischemia), the IMD 502 may enter an emergency mode. For example, in the emergency mode, the IMD 502 may take action to protect the user (for example to increase blood flow and/or stabilize cardiac activity). Alternatively or additionally, in the emergency mode, the IMD 502 may lower security and/or allow emergency and/or medical personnel to make short term changes in the functioning of the IMD 502. Optionally, the IMD 502 may have a memory (read only and/or read write) that stores certain actions that are allowed in one or more emergency situations with reduced security. Optionally the IMD 102 may have a computer readable memory (for example a RW and/or RO memory) that stores the restore and/or default and/or current parameter values that can be restored after the temporary parameters expire and/or the emergency situation changes. Optionally, the IMD 102 may include a real time clock. For example the clock may be used to determine when a parameter value has expired and/or should be changed. In some embodiments, an IMD 502 may have a safe mode. For example, when the IMD 502 detects that it is in a safe location (for example a location of a recognized hospital and/or a home of the user). In the safe mode, the IMD 502 may have a lowered security allowing programming and/or data transfers that would not be allowed in the normal mode and/or with reduced security measure than in the normal mode. Optionally, the security protocols will remain unchanged, but certain functions may be assigned to different security levels according to a secondary condition. For example a secondary condition may include a location and/or a condition of the subject and/or a time.

In some embodiments, different commands and/or actions may require different levels of security. For example, a command to change a setting of the IMD 502 that may in a short term cause significant harm and/or danger to the user may require the highest level of security. For example, a long term change is a setting of the IMD 502 that could cause danger and/or harm to the user may require a high level of security. For example, a short term change in a setting of the IMD 502 and/or a change that is unlikely to cause significant harm or danger to a user may require a medium level of security. For example, communication of health and/or sensitive data may require a medium level of security. For example, communication of non-sensitive data (for example a battery level) may require low level of security.

In some embodiments, a different level of security may require a different security protocol. For example, a message at the highest security may require individual verification over the TET channel 513. Alternatively or additionally, a message at the highest security may be allowed on a two way channel 510 when the security key is fresh (for example when the security key was fixed based on a communication over the TET channel within the last minute and/or within the last 10 minutes and/or within the last half hour and/or within the last six hours). Optionally, a message at a high level of security may be accepted based only on the security of the two way channel 510 and/or with an older security key than the highest security level, for example when the security key was fixed based on a communication over the TET channel within the within the last 10 minutes and/or within the last half hour and/or within the last six hours and/or within the last day and/or if the device has been in a safe location since the last security key refresh. Optionally, for medium and/or low level security an older key may be acceptable and/or even a non-secured communication link may be used.

In some embodiments, verification and/or key transfer on the TET channel may be secured by authentication. Optionally, authentication of TET communications may be required for high level security actions. For example, authentication may include requiring the TET channel to transfer a large amount of power and/or energy and/or to transfer power over a long time (something that may be particularly difficult for a malicious intruder). Alternatively or additionally, authentication may require use of a code or another verification of the identity of the ED 504. Alternatively or additionally, authentication may include security verification over the two-way channel before accepting a security key over the TET. In some embodiments, the verification 571 may include the ED 504 sending a parameter value to the IMD 504 over the TET 513 link. In some embodiments, verification will include repeating a parameter value sent over the two way channel 510. Alternatively or additionally, a command may be given over the two way channel 510 to change a parameter value and the new value may be given over the TET link 513. Alternatively or additionally, a value may be given over the two-way channel 510 and a message defining which parameter to change may be sent over the TET link 513. In some embodiment, an authentication may include a requirement of an operator identification. For example, an ED 504 may include a bio-metric device and/or an input device for identifying an operator. In some embodiments, an IMD 502 will allow a temporary change of state and/or therapeutic parameter prior to verification. For example, when verification is received in time, the new state may be preserved. Optionally, when verification is not received in a predetermined time, the IMD 502 may revert back to a previous state and/or parameter.

Figure 5B:
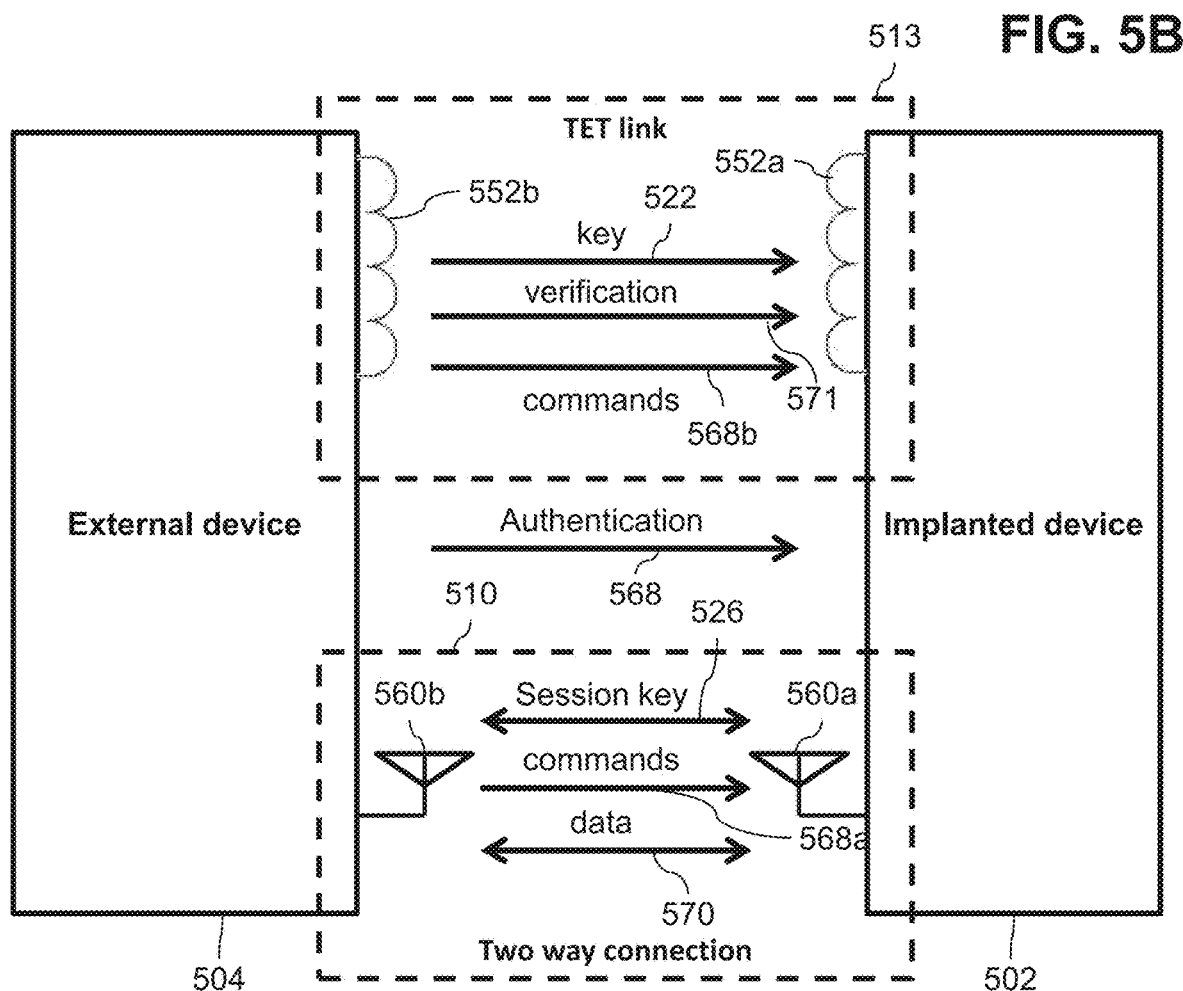

FIG. 5B is a schematic diagram illustrating signal flow and/or security protocols in accordance with an embodiment of the current invention. In some embodiments, a one-way communication channel over a short range TET link 513 is used for transferring 522 an encryption key for encryption of a message. The message may include, for example a session key 526 and/or a command 568*a* and/or data 570 transmitted between an ED 504 and an IMD 502 over a two way communication channel 510. Alternatively or additionally, the one-way communication TET link 513 may be used for verification 571 of a message sent from the ED 504 to the IMD 502 and/or for sending a command 568*b* from the ED 504 to the IMD 502. In some embodiment, communication over a TET is further protected by a authentication 568 protocol.

In some embodiments, a TET link 513 may be used for verification of a message over the two way channel 510. For example, when ED 504 gives a highly sensitive command (for example a command to change a treatment parameter of the IMD 502) the IMD 502 may require verification over the TET link 513. For example, verification 571 may include a simple statement verifying that the ED 504 sent a command 568*a* over the two way channel 510. Alternatively or additionally, the verification message may include a password and/or a time stamp and/or a packet ID number that identifies the message from the two way link 510.

In some embodiments, a session on the two way link 510 may have multiple security keys that change from time to time and/or according to instructions passed over the TET link 513 and/or according to instruction passed over an encrypted conversation in the two way channel 510 and/or according to stored data shared between the IMD 502 and the ED 504. Switching of session keys from time to time may make it harder to break the encryption of the two way channel 510 by statistical means.

In some embodiments, the IMD 502 may periodically send a list of settings and/or treatment parameters to the ED 504. For example the data may be checked periodically to make sure that no settings were inadvertently and/or maliciously mis-set.

In some embodiments, a limited range of changes in treatment settings of the IMD 502 may be permitted with a relatively low level of security while other changes may require higher security. For example, the IMD may include a read only and/or a read write memory with stored ranges of settings that are allowed with relatively low security. Alternatively or additionally, relatively small changes in parameters may be allowed with lower security than a larger change.

In some embodiments the TET link 513 may include an inductive channel. For example a signal and/or energy may be sent from an inductor (for example a coil 552*b*) of the ED 504 to an inductor (for example a coil 552*a*) of the IMD 502. In some embodiments, the two-way channel 510 may include a radio channel. For example radio signals may be sent back and forth between a transceiver 560*a* of the IMD 504 and a transceiver 560*b* of the ED 504. Optionally, transceiver 560*a* may include a dedicated antenna. Alternatively or additionally, transceiver 560*a* may use coil 562*a* as an antenna.

FIG. 6 is a block diagram of an IMD 602 in accordance with an embodiment of the current invention. In some embodiments, an IMD 602 includes a therapeutic unit 682 and/or a sensor unit 690. For example, a therapeutic unit may include actuators 686*a* 686*b* that apply therapies to tissue. For example, the sensor unit 690 may include sensors 688*a* 688*b* which sense a condition of a user of the device.

In some embodiments an IMD 602 may be encased in a protective cover 672 (for example cover 672 may be water proof, biocompatible, protect the user from the internal parts of the IMD and/or protect the user from electric shock and/or to protect internal parts of the IMD 602 from body fluids and/or to protect the IMD from physical damage for example knocks). Optionally one or more sensors (for example sensor 688*a*) are inside cover 672. For example, sensor 688*a* may sense a magnetic field. Alternatively or additionally, a sensor that extends outside of cover 672 (for example sensor 688*b*). For example, sensor 688*b* may include an electrode, pressure transducer, a thermocouple and/or a flow meter.

In some embodiments, one or more actuators (for example actuator 686*a*) are inside cover 672. For example, an actuator 688*a* may produce a magnetic field. Alternatively or additionally, an actuator that extends outside of cover 672 (for example actuator 686*b*). For example, actuator 686*b* may include an electrode, an ultrasound transducer and/or a heating element. In some embodiments a single element may serve both as a sensor and an actuator. For example, an electrode may be used to collect information about electrical signal inside the user and/or also apply an electrical signal. For example, IMD may include a pacemaker and/or an implantable cardiac defibrillator (ICD) and/or a cardiac contractility modulation (CCM) device. For example, the device may apply pacing signals and/or non excitory signals at various periods of the cardiac cycle.

Figure 7:
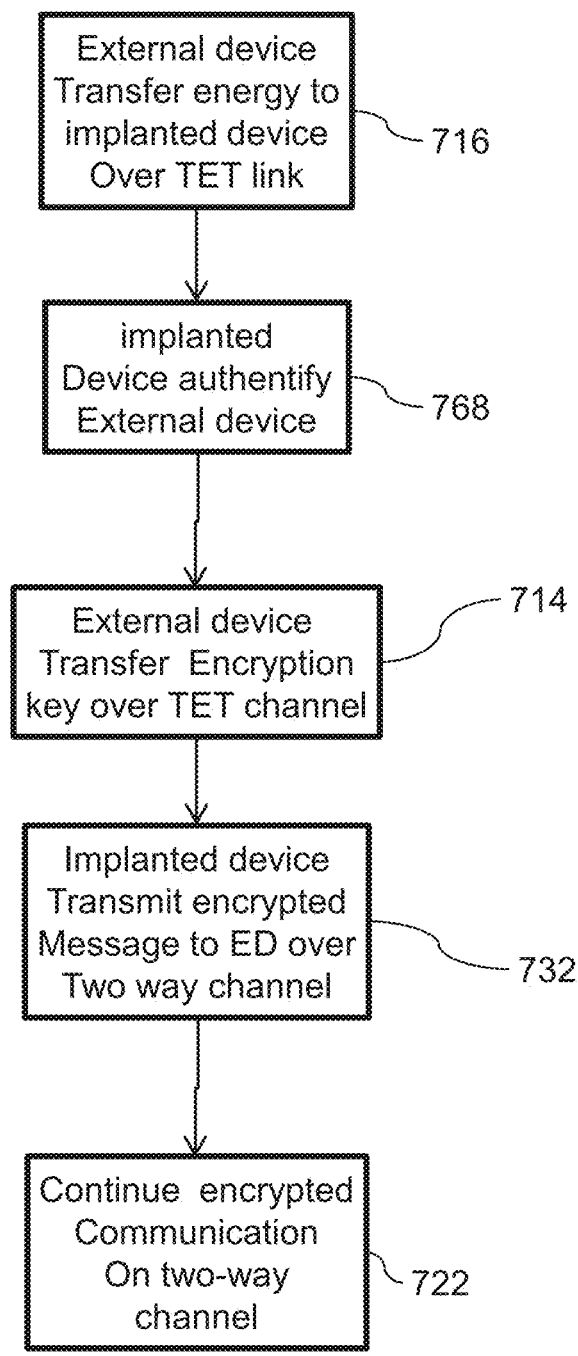
FIG. 7 is a flowchart illustration of a method of securing a communication in accordance with an embodiment of the current invention.

FIG. 7 is a flowchart illustration of a method of securing a communication in accordance with an embodiment of the current invention. In some embodiments, an infiltration resistant TET channel will be used protect an IMD from being controlled by a malicious device and/or to protect communication between an IMD and an ED. For example, the infiltration protected TET channel will be used to transfer a public key to the IMD that will be used to prevent an attacker from infiltrating communication over a less protected channel (for example by encrypting communication over the less protected channel). Optionally, the TET channel may be configured for one way communication and/or the less protected channel may be configured for higher speed communication and/or two way communications.

In some embodiments, an external device will transfer energy 716 to an implanted device. For example the energy transfer may include power for charging a battery of the IMD. Optionally the energy transfer link may be over a channel that decays quickly over distance. Optionally, in order to spoof signals over the energy transfer link a malicious device may require high power and/or a position very close to the IMD. For example the link may lose more than 25% of its power over 10 cm and/or more than 50% of its power over 50 cm and/or more than 90% of its power over two meters. For example, the energy transfer may be over a TET link. For example, the TET link may include an inductive coupling.

In some embodiments, the IMD may authenticate 768 that the ED is legitimate device. For example, authentication may include requiring the ED to transfer a certain quantity of energy and/or power and/or to transmit power over a minimal time span. Alternatively or additionally, further authentication methods may be used.

In some embodiments, the ED may use the TET link to transfer 714 an encryption key to the IMD. For example, the ED may transfer a public key of asymmetric encryption to the IMD. Optionally the IMD will encrypt a message with the encryption key supplied by the ED. For example, the message may be sent from the IMD to the ED over a two-way communication medium. In some embodiments, the IMD will encrypt a session key using the encryption key supplied from the ED and/or transfer 732 the encrypted session key over the two-way communication medium to the ED. Further communication 722 will optionally proceed over the two-way using symmetric encryption based on the session key.

In some embodiments, security of continued communication on the two-way medium will be boosted using the TET link. For example, the ED may periodically send a new encryption key over the TET link and/or the new key will be used to refresh the old encryption keys, for example by encrypting and transferring a new session key. Alternatively or additionally, the TET link may be used to verify communications received from the ED. Alternatively or additionally, only a partial message may be sent over each medium. For example, the TET link may be used to transfer certain data such that the messages on either medium are not enough to understand the full message and/or carry out the instructions being communicated. For example, a message sent over the two-way link may lack a necessary parameter value that is sent over the TET link.

Figure 8A:
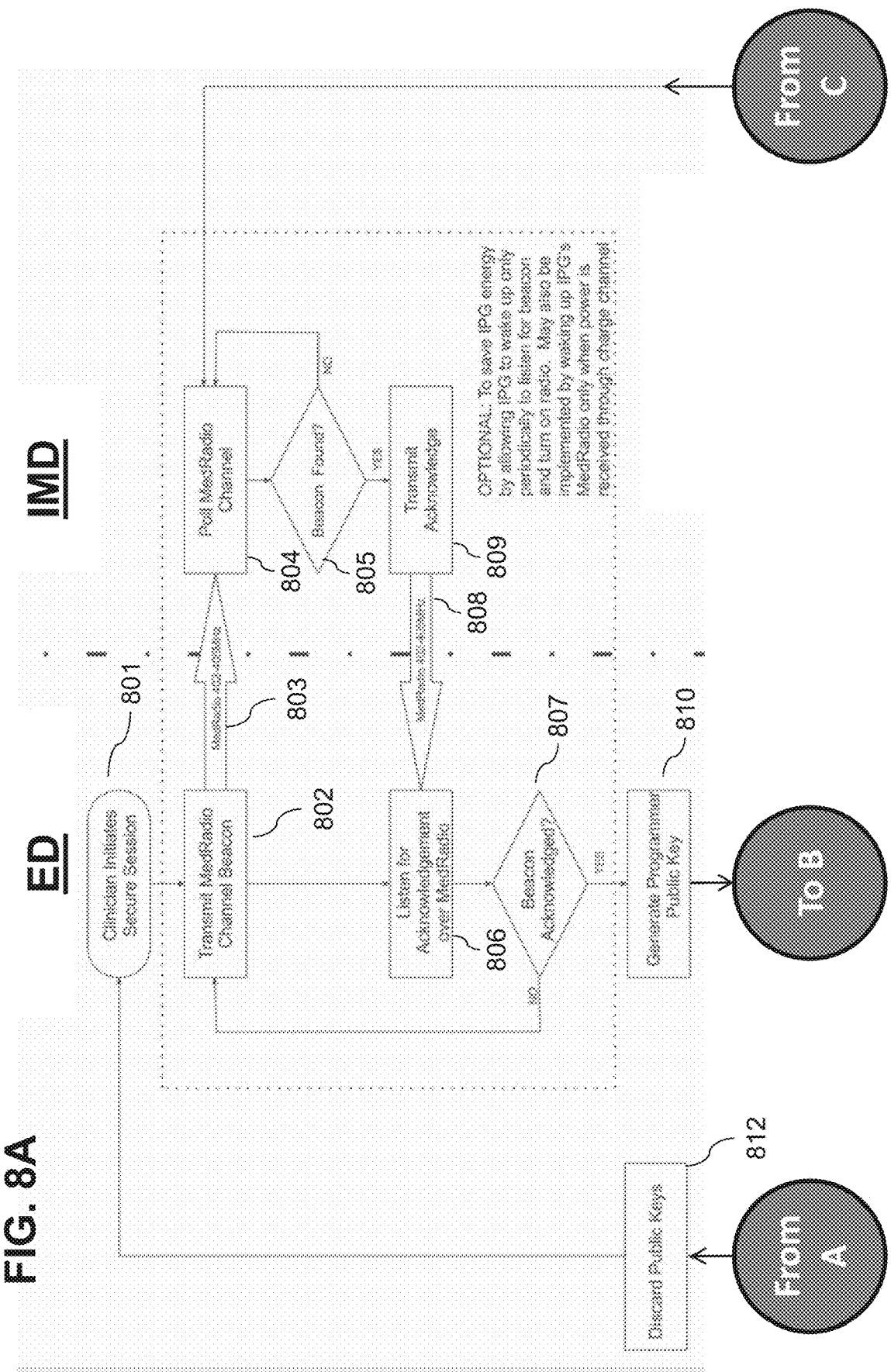
Figure 8B:
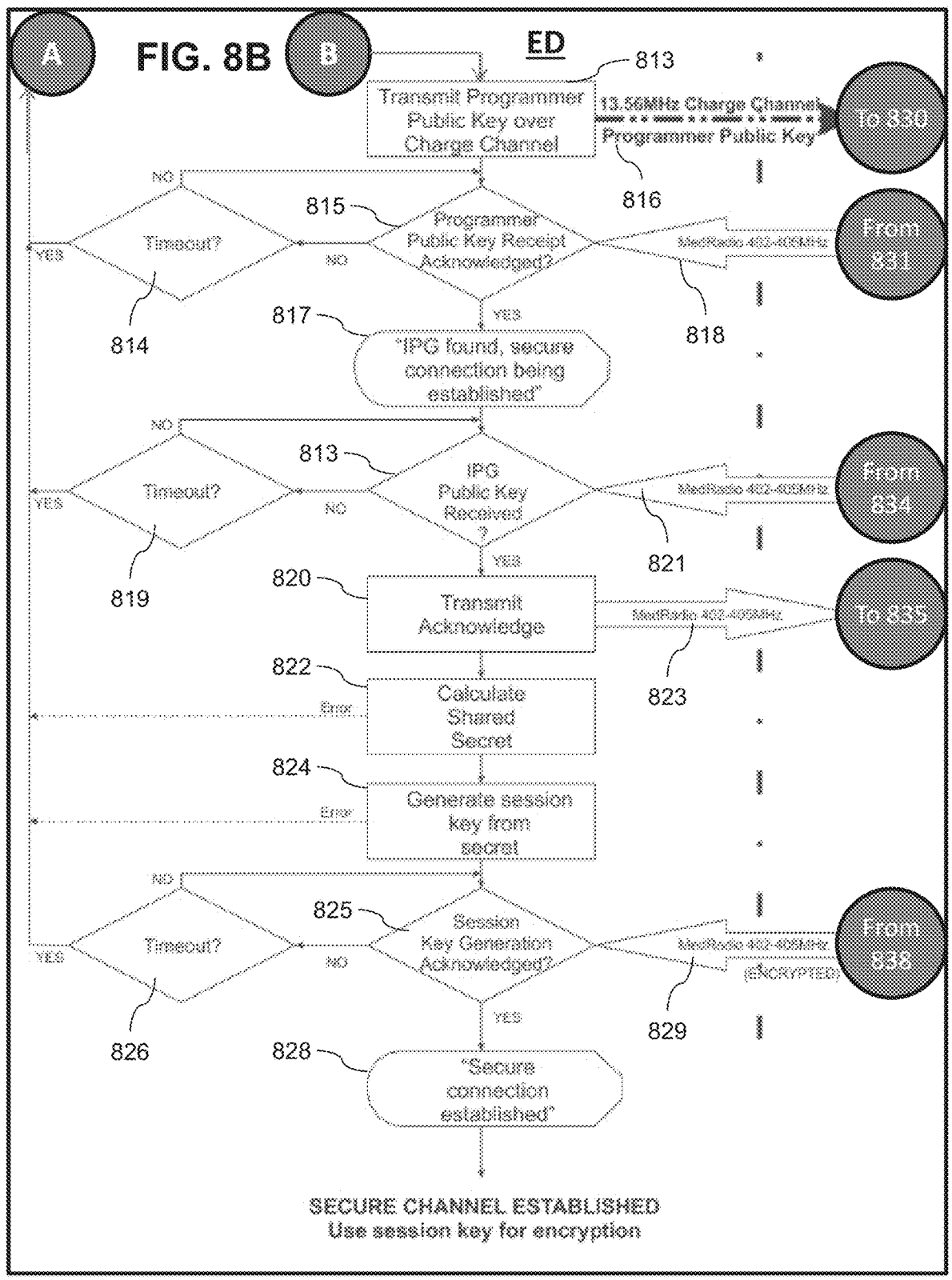

FIGS. 8A-8C illustrate an example of communication between an ED and an IMD in accordance with an embodiment of the current invention.

In some embodiments, a clinician initiates 801 a secure session. For example, the clinician moves the ED to a position alongside a subject near a location where the IMD is implanted. For the ED may be held within 10 cm of the IMD. A communication link may open automatically as a result of the proximity of the ED to the IMG. Alternatively or additionally, the clinician may activate the ED and/or the clinician may initiate charging the IMD over a TET link. Alternatively or additionally, the IMD may remain active polling 504 a communication channel 803 (without an external initiation).

In some embodiments, the session begins with the ED transmitting 802 a beacon signal 803 to the IMD. Optionally the signal may be a MedRadio signal (e.g. a 402-405 MHz signal). Optionally, the IMD is periodically polling 804 for the beacon. Alternatively or additionally, the ED may activate the communication of the IMD. For example the IMD may include a reed switch which is activated by a magnet in the ED and/or over the TET link. Optionally, after transmitting 802, the beacon, the ED listens 806 for an acknowledgement.

In some embodiments, when the IMD is activated and/or has received 805 the beacon signal 803 the IMD sends 809 an acknowledgement signal 808 to the ED. For example, the acknowledgement may be over the MedRadio channel and/or another medium.

In some embodiments, when the ED receives 807 the beacon acknowledgement 808, a public key is generated 810 and sent 813 to the IMD. For example the key is sent 513 over a secure channel 816. Optionally, the secure channel 816 includes a medium on which it would be difficult for an intruder to transmit a counterfeit message. For example, example the secure channel 816 may require very short range between the transmitter and the IMD and/or may require high power levels and/or may require long connection time. For example, the secure channel 816 may include a TET channel, for example a 13.56 MHz charge channel. Optionally, when the IMD receives 830 the public key, it transmits 831 an acknowledgement 818 to the ED. Optionally upon receiving 815 the acknowledgement 818, the ED displays 817 a message to the clinician, for example "IPG found secure connection being established." Optionally, if an acknowledgement 818 is not received 815 within a timeout 814 period, then the ED discards 812 current public keys and waits for initiation 801 of a new session by the clinician. If the public key is not in not received 830 in a timeout period 832 the IMD optionally returns to the polling 804 state.

In some embodiments, after transmitting 831 acknowledgement of receipt of the public key, the IMD generates 833 a public key and/or transmits 834 the public key 821 to the ED. For example, key 821 may be transferred over the MedRadio channel. The IMD optionally waits 835 for an acknowledgement 823 of receipt of the public key 821. For example, the ED may transmit 820 acknowledgement 823 of receipt of the public key over the MedRadio channel. If there is an error, the system optionally returns to the waiting state, e.g. waits for the clinician to initiate 801 a new session. Optionally, if a key 821 is not received 813 within a timeout 819 period, the ED discards 812 current public keys and waits for initiation 801 of a new session from the clinician.

In some embodiments, after exchange of public keys, the IMD and/or the ED generate 822, 836 a shared secret. Optionally the shared secret is used to generate 824, 837 a session key. The session key is optionally used to encrypt further communication. For example, the IMD may transmit 838 an encrypted acknowledgement 829 of generating 837 the session key. If there is an error 825, for example the session key of the ED fails to decrypt the acknowledgement 829 of the IMD and/or the acknowledgement 829 is not received within a timeout 826 period, then the public keys may be discarded 812 and/or the system may return to wait for new instructions to initiate 801 a secure session from the clinician. Once the secure session is established, the ED optionally displays 828 a success message to the clinician and/or communication continues using the session key. Alternatively or additionally, the ED may send an acknowledgement of successful generation of the session key to the IMD.

It is expected that during the life of a patent maturing from this application many relevant communication media and/or protocols will be developed and the scope of the terms radio channel and encryption is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When two ranges are connected with an and/or connector then the ranges may be separate and/or continuous. For example if a parameter is said to range between 1 to 3 and/or between 3 to 5 and/or 5 to 7 then the ranges 1 to 5 and 5 to 10 and 1 to 10 are also included.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of secure communication between an implanted device and an external device comprising:
    transferring energy over a transcutaneous energy transfer (TET) link to the implanted device by the external device, said TET link configured to charge a power supply of the implanted device;
    modulating an encryption key onto said TET link by said external device;
    said implanted device retrieving said encryption key from said modulating of said TET link; and
    encrypting communication including at least one of control commands and performance parameters for the implanted device over a radio channel which is separate from said TET link using said encryption key.

2. The method of claim 1, wherein the radio channel includes a range at least twice as large as the TET link.

3. The method of claim 1, wherein the TET link uses at least twice as much power for a transmission as the radio channel.

4. The method of claim 1, wherein the TET link requires at least twice as time for a transmission as the radio channel.

5. The method of claim 1, wherein said transferring energy further includes:
    inducing a current in an implanted device by the external device.

6. The method of claim 1, further comprising:
    charging a battery of said implanted device with said transferred energy.

7. The method of claim 1, wherein said encryption key is a public key and wherein said encrypting includes transmitting a message from said implanted device over said radio channel using asymmetric encryption and said public key.

8. The method of claim 7, wherein said message includes a session key, the method further comprising:
    encrypting a command to said implanted device with said session key.

9. The method of claim 7, wherein said message includes a session key, the method further comprising:
    encrypting data sent from said implanted device with said session key.

10. The method of claim 1, further comprising:
    securing a command sent to said implanted device according to a high level security protocol; and
    securing data sent from said implanted device to an external device according to a low level security protocol.

11. The method of claim 10, wherein a command from said external device to said implanted device to change a treatment parameter is assigned said high security level.

12. The method of claim 11, wherein said command is temporarily assigned said low security level in response to a condition of a user of the implanted device.

13. The method of claim 12, wherein said condition includes a cardiac infarction.

14. The method of claim 10, wherein said high level security protocol requires modulation of a renewed encryption key within 15 minutes before accepting said command.

15. The method of claim 1, further comprising:
    verifying a message sent over said unsecured radio channel by sending a verification message from said external device to the implanted device over said TET link.

16. The method according to claim 1, wherein said TET link comprises an inductive coupling.

17. The method according to claim 16, wherein said inductive coupling is via a first inductance coil configured as part of said external device and a second inductance coil configured as part of said implanted device.

18. The method according to claim 1, comprising said implanted device storing said encryption key.

19. An implanted device for secure communication comprising:
    a transcutaneous energy transfer (TET) receiver configured for receiving power from an external device and supplying said power to the implanted device;
    a data receiving circuit connected to said TET receiver configured to receive a public key from said TET receiver, said public key modulated onto a power transmission;
    an encryption module functionally connected to said data receiving circuit for receiving said public key from said data receiving circuit and configured for encrypting a message with asymmetric encryption based on said public key to produce an encrypted message, and
    a transceiver functionally connected to receive said encrypted message from said encryption module and send said encrypted message to said external device over a two way radio channel.

20. The device of claim 19, wherein the implanted device does not include a modulator capable of modulating an outgoing message onto said TET channel.

21. The device of claim 19, wherein the implanted device does not include an asymmetric decryption circuit capable of generating said public key and a private key and decrypting an asymmetric encrypted message encrypted with said public key.

22. The device of claim 19, further comprising a rechargeable power supply for said implanted device, said power supply functionally attached to said TET receiver for recharging from said power supplied by said external device.

23. The device of claim 19, wherein said external device includes a TET generator configured to transmit energy to the implanted device and an asymmetric decryption circuit capable of generating said public key and a private key and decrypting an asymmetric encrypted message encrypted with said public key and a modulator functionally connected to said decryption circuit for receiving said public key and said modulator functionally connected to said TET generator for modulating said public key onto a TET signal and transferring said key to the implanted device.

24. The device of claim 23, wherein said external device does not include a receiver capable of receiving a message over said TET channel.

* * * * *